United States Patent
Meyers (12) 
(10) Patent No.: US 6,245,569 B1
(45) Date of Patent: Jun. 12, 2001

(54) METHOD FOR EVALUATING REACTION PROFILES

(75) Inventor: Wilfried Meyers, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/030,887

(22) Filed: Feb. 26, 1998

(30) Foreign Application Priority Data

Feb. 27, 1997 (DE) .............................................. 197 07 897

(51) Int. Cl.$^7$ ..................................................... G01N 33/00
(52) U.S. Cl. ..................... 436/34; 422/73; 422/82.05; 436/55; 436/69; 436/70
(58) Field of Search ..................... 422/68, 1, 73, 422/82.05; 436/34, 55, 69, 70, 183

(56) References Cited

U.S. PATENT DOCUMENTS

| | | |
|---|---|---|
| 3,635,678 | 1/1972 | Seitz et al. . |
| 4,454,752 | 6/1984 | Scordato . |
| 4,472,505 | 9/1984 | Manabe et al. ......................... 436/47 |
| 4,492,462 | 1/1985 | Pross et al. . |
| 4,822,568 | 4/1989 | Tomita . |
| 5,232,668 | * 8/1993 | Grant et al. ......................... 422/82.05 |
| 5,885,839 | * 3/1999 | Lingane et al. ......................... 436/34 |

OTHER PUBLICATIONS

H. Oishi et al, Chem. Pharm. Bull. 1988, 36, 3012–3019, Aug. 1988.*
I. Andersen et al. *Scand. J. Clin. Lab, Invest.* 1977, 37, 7–13.*
M. F. Scully et al, *Clin. Chim. Acta* 1977, 79, 595–602.*
S. A. Morrison *Biochemistry* 1983, 22, 4053–4061.*
H. Oishi et al, *Chem. Pharm. Bull.* 1988, 36, 3012–3019.*
H. Kolde, "Chromo TimeSystem—a New Generation of Coagulation Analyses", Behring Inst. Mitt., 78:176–187 (1985).

* cited by examiner

*Primary Examiner*—Arlen Soderquist
(74) *Attorney, Agent, or Firm*—Finnegan, Henderson, Farabow, Garrett and Dunner, L.L.P.

(57) ABSTRACT

Accurate evaluation of reaction kinetics is evaluated using the threshold-value method. Amenable curve profiles for this method occur whenever, under controlled ambient conditions, the transition of a reaction-dependent variable from an initial state to a final state is observed over time.

13 Claims, 17 Drawing Sheets

METHOD FOR EVALUATING REACTION PROFILES

The invention relates to a method for the accurate evaluation of reaction kinetics, which are evaluated using the so-called threshold-value method. Curve profiles of this type occur whenever, under controlled ambient conditions, the transition of a reaction-dependent variable from an initial state to a final state is observed over time.

The threshold-value method is a method which is frequently used in practice. A method of this type is, for example, described by KOLDE (Behring Inst. Mitt. 78, p. 176–187 (1985)).

A way of characterizing an object to be measured on the basis of a specific measuring system using a 2-step method has already been described. In this case a) by adding certain activation components in the object to be measured, a process is initiated which delivers a signal over time on the basis of a defined detection principle. This gives a series of measurements $(T_i, S_i)$, i=1, . . . ,n. In this case, $T_i$ denotes the time of the i-th instant and $S_i$ denotes the signal at time $T_i$.

b) The series of measurements $(T_i, S_i)$ i=1, . . . ,n is reduced with the aid of a transformation f to a raw value R:

$$(T_i, S_i), \quad i = 1, \ldots, n \xrightarrow{f} R$$

The threshold-value method is such a transformation f as is needed in step b). It is essentially characterized by a parameter d which establishes the actual threshold to be used. The raw value is in this case defined as the time at which, starting from a base value, the series of measurements persistently exceeds the threshold for the first time.

Figure 1:
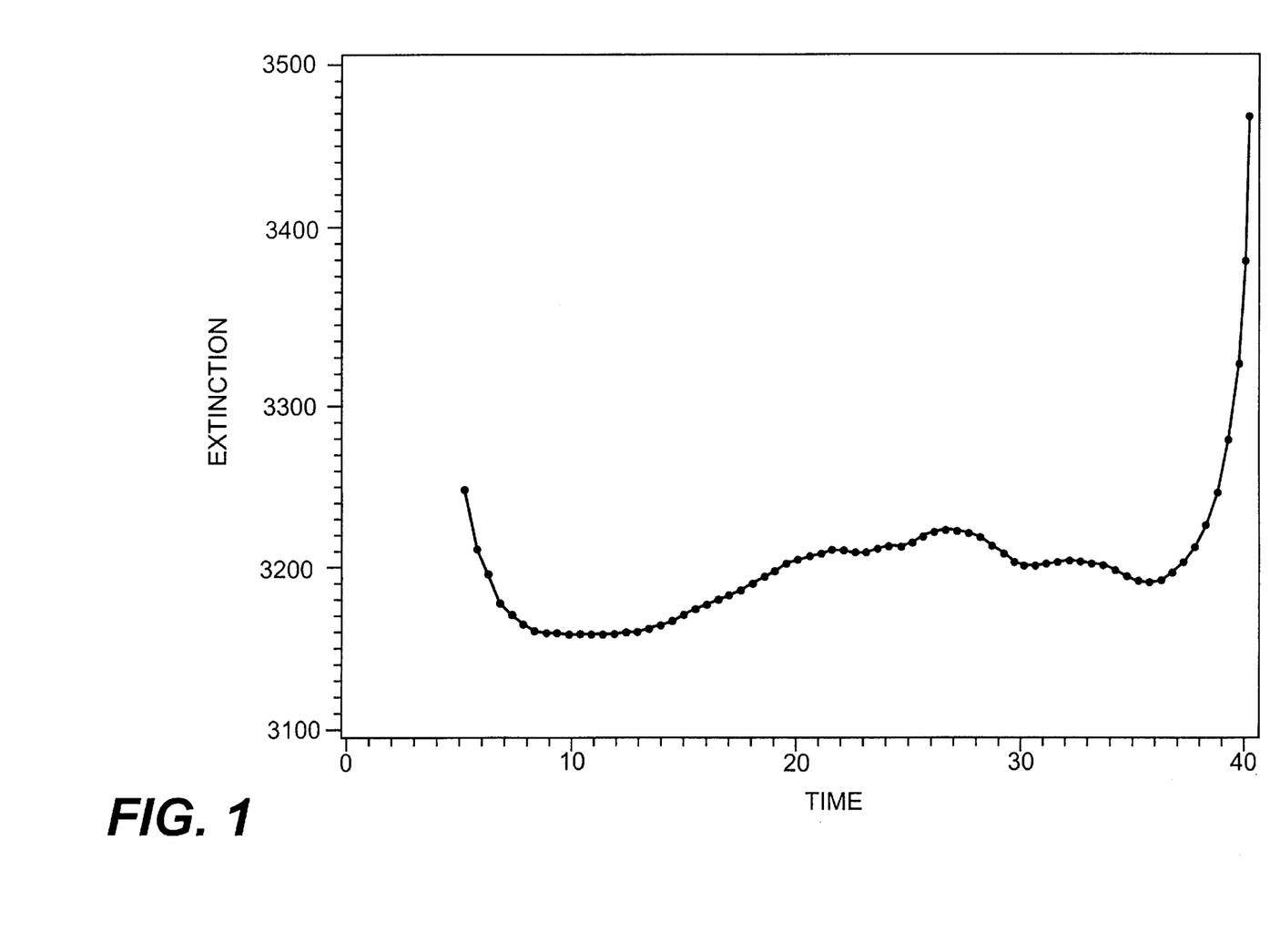
FIG. 1: Extinction v. Time having an inconsistent profile.

The known method cannot correctly evaluate curve profiles which have an inconstant profile, as represented in FIG. 1. In the example given in this figure, the correct raw value would have been about 38 s (persistent exceeding of a predetermined threshold), but was actually determined at about 25 s using the known method. Depending on the field of application, a miscalculation of this type may have serious consequences and even, in the extreme, lead to life-threatening situations (see examples).

The object of the present invention was therefore to provide a method which eliminates the abovementioned disadvantages. This means that miscalculations, as may arise when using the described method, can be made as improbable as is technically feasible.

BRIEF DESCRIPTION OF THE DRAWINGS

FIG. 4l: Extinction v. Time having Q=207.53.

The solution to this problem is provided by the embodiments described in the patent claims. It has unexpectedly been established that the problem can be solved by changing step b) in the above-described method. The step described there, namely that of applying a fixed operator f to the series of measurements, is to be replaced by a sequence of steps, in which a different operator is always to be used and the raw values thus obtained are subject to a plausibility check. The interchanging of the operators, and the consequent correct evaluation of the operators, is carried out automatically using the data-processing facility of the measuring system, using specific preset parameters. These parameters are specific to the equipment and reaction and can be determined by the person skilled in the art using simple preliminary tests. It has unexpectedly been established that the following configuration is particularly advantageous since it can be used for many equipment/reaction combinations:

$d_{max}$=1.5 to 10×$d_0$, more preferably about 2×$d_0$
n=5 to 30, more preferably about 10
$Q_0$=5 to 50, more preferably 15 to 30, in particular more preferably about 20.

In this case, only $d_0$ is then directly dependent on the measuring system.

The method can, for example, be carried out as follows:

a) values, specific to the reaction, of an initial value $d_0$ and of a maximum value $d_{max}$ (>$d_0$) as well as a step number n and hence a step size $d_s=(d_{max}-d_0)/n$ are established;

b) for the range from d=$d_0$ to $d_{max}$, the value $T_n$ is determined for each $d_n=(d_0+(d_s)*n)$, c) from the ordered series of values $T_0$ to $T_{max}$, the differences $D_i=T_i-T_{i-1}$ are taken for i=1, . . . ,n, and the largest value $D_{max}$ and the smallest value $D_{min}$ from the set $D_1, \ldots, D_n$ are determined, and the ratio $Q=D_{max}/D_{min}$ is taken, d) only measurements for which $Q \leq Q_0$ are used for further evaluation, measurements for which $Q > Q_0$ being discarded as too inconstant.

The parameters to be set in this method are as follows:
$d_0$—initial threshold
$d_{max}$—maximum threshold
n—step number (integer>0)
$Q_0$—limit value for the ratio Q ($Q_0$>0)

One configuration which could be used in a number of situations is:
$d_{max}=2 \cdot d_0$
n=10
$Q_0$=20

With a suitable configuration, the method according to the invention can avoid miscalculation of the raw value using the "threshold-value method" operator, with the greatest likelihood that can be achieved technically. It thus provides improved reliability in terms of correct characterization of the object to be measured.

Figure 2:
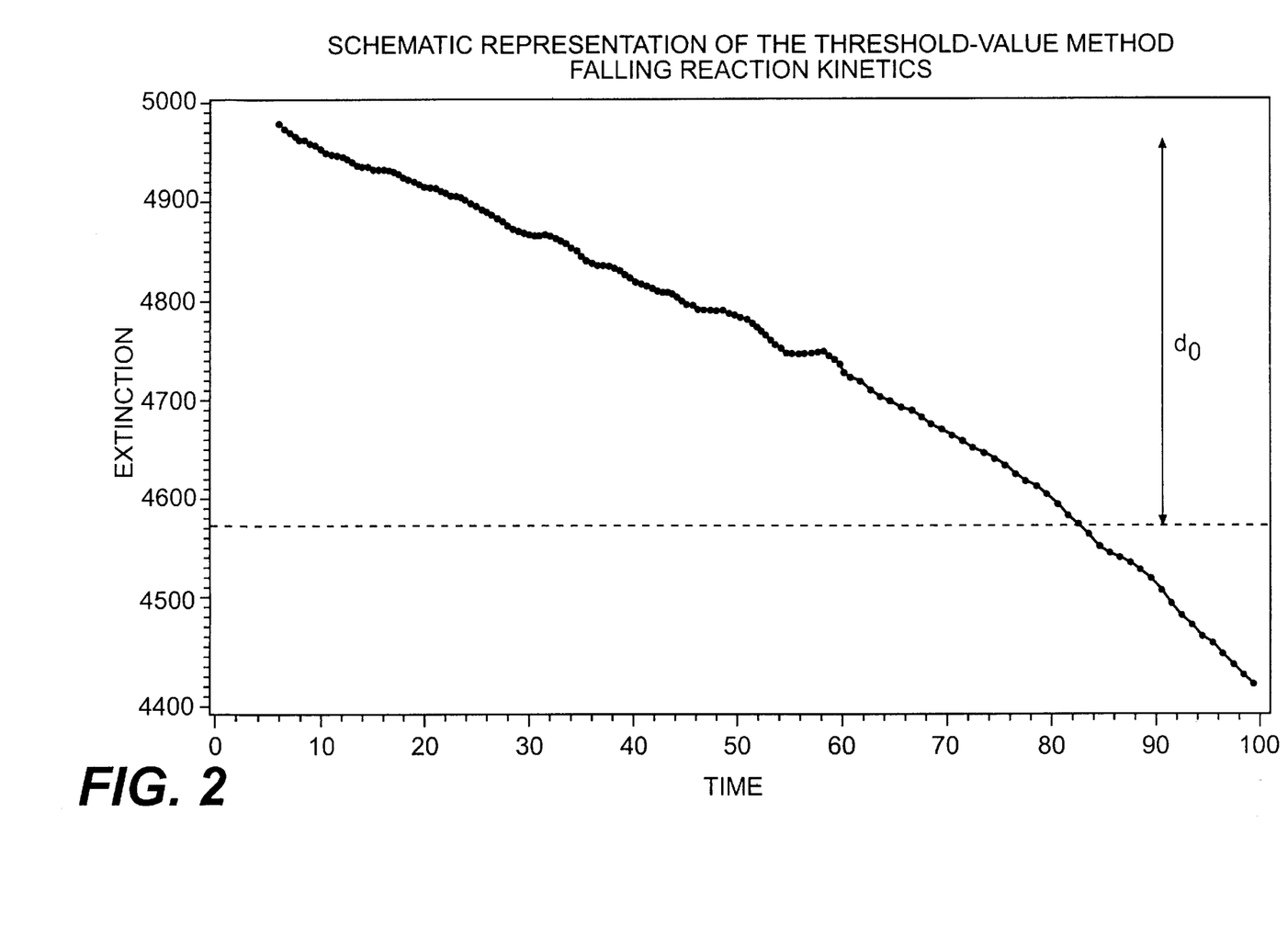
FIG. 2: Extinction v. Time having decreasing extinction.
Figure 3:
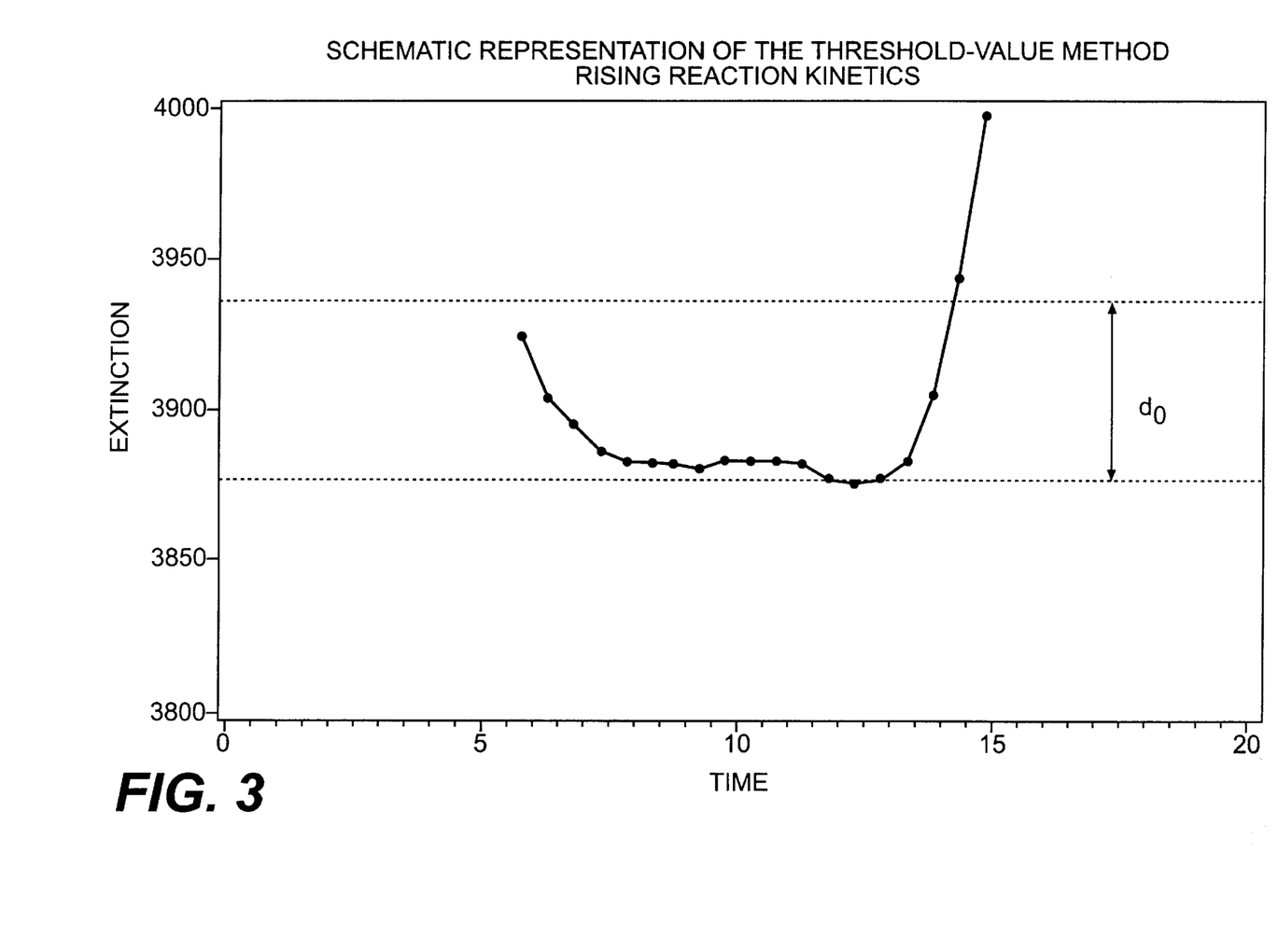
FIG. 3: Extinction v. Time having increasing extinction.
Figure 4A:
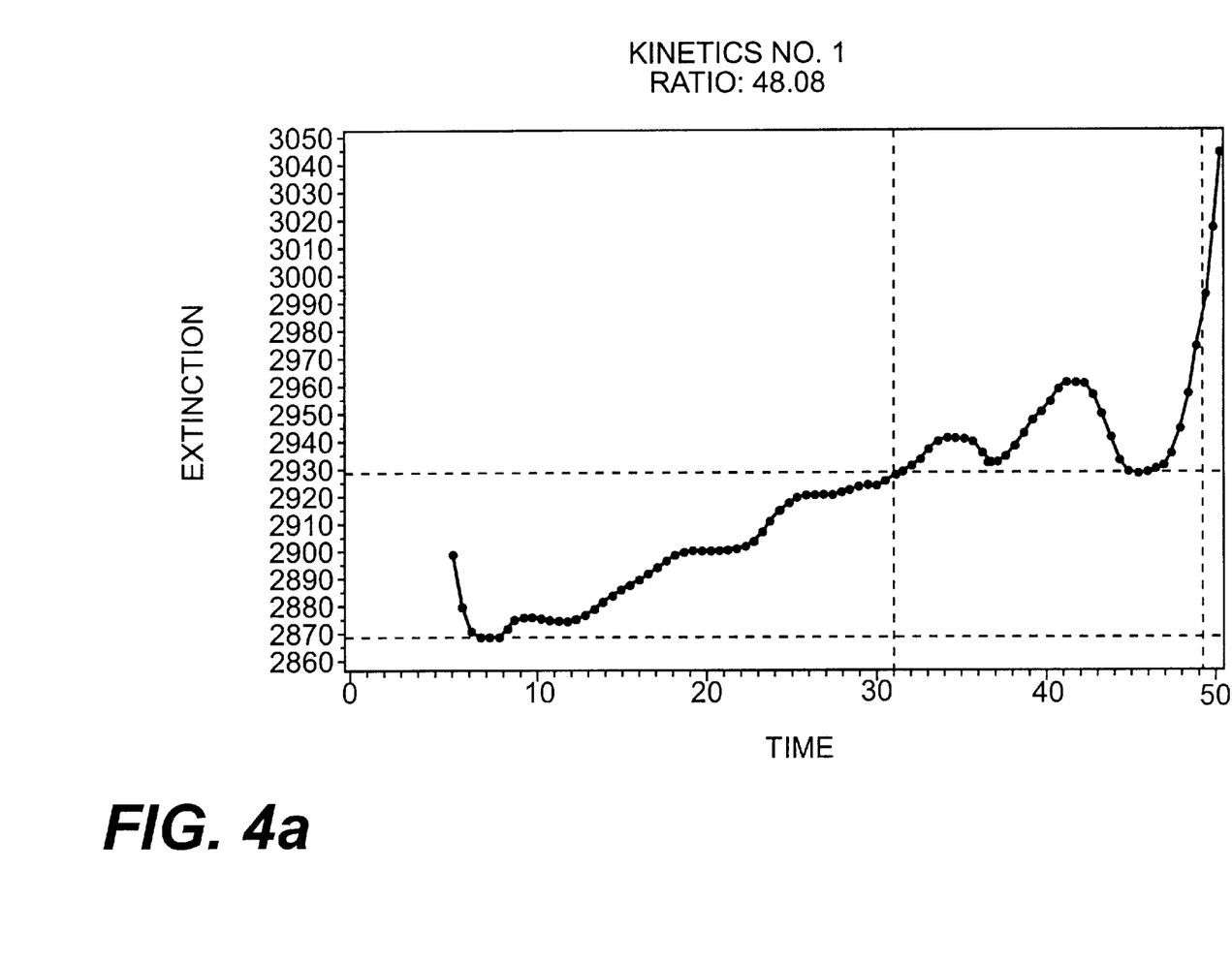
FIG. 4a: Extinction v. Time having Q=48.08.
Figure 4B:
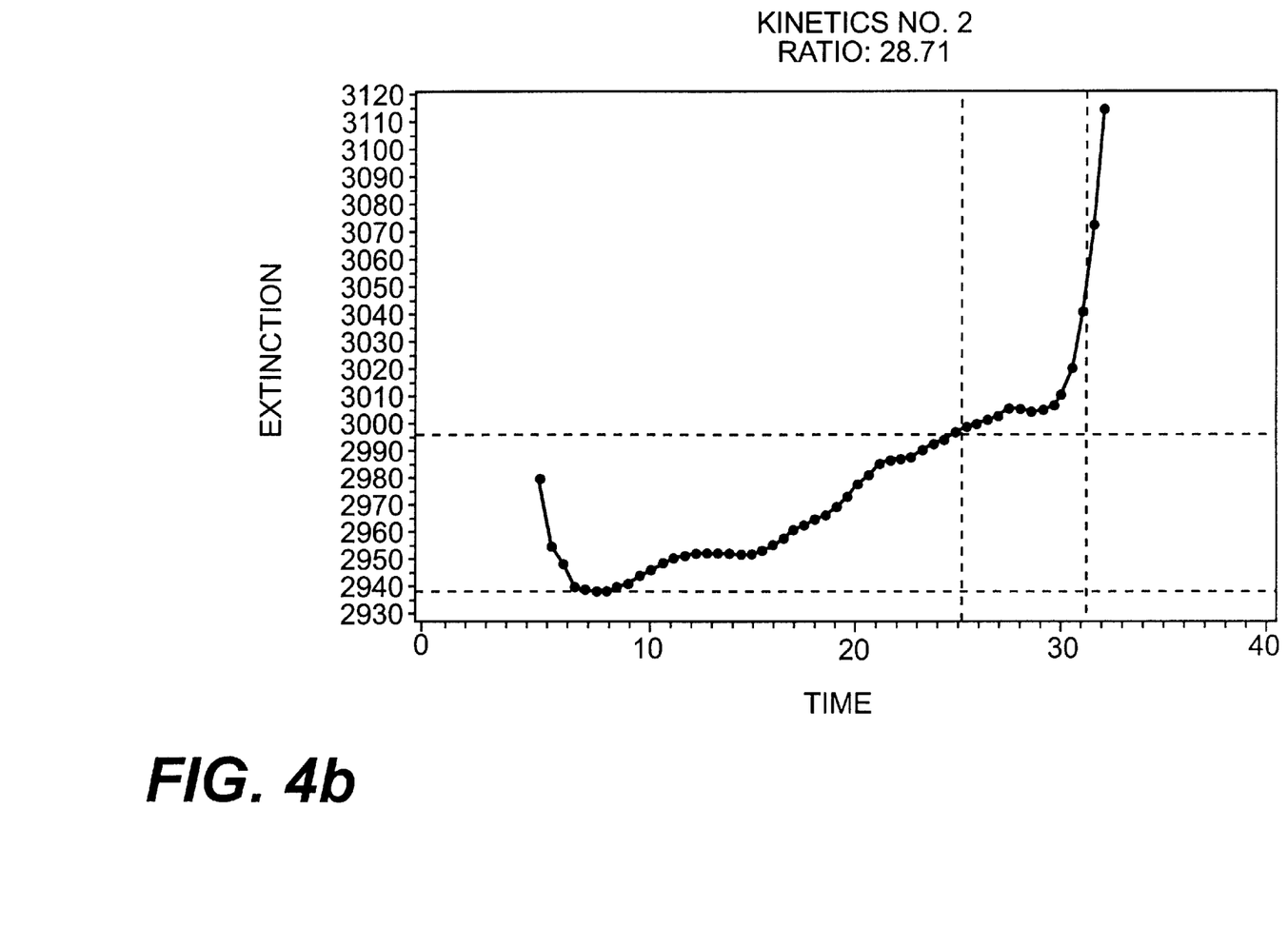
FIG. 4b: Extinction v. Time having Q=28.71.
Figure 4C:
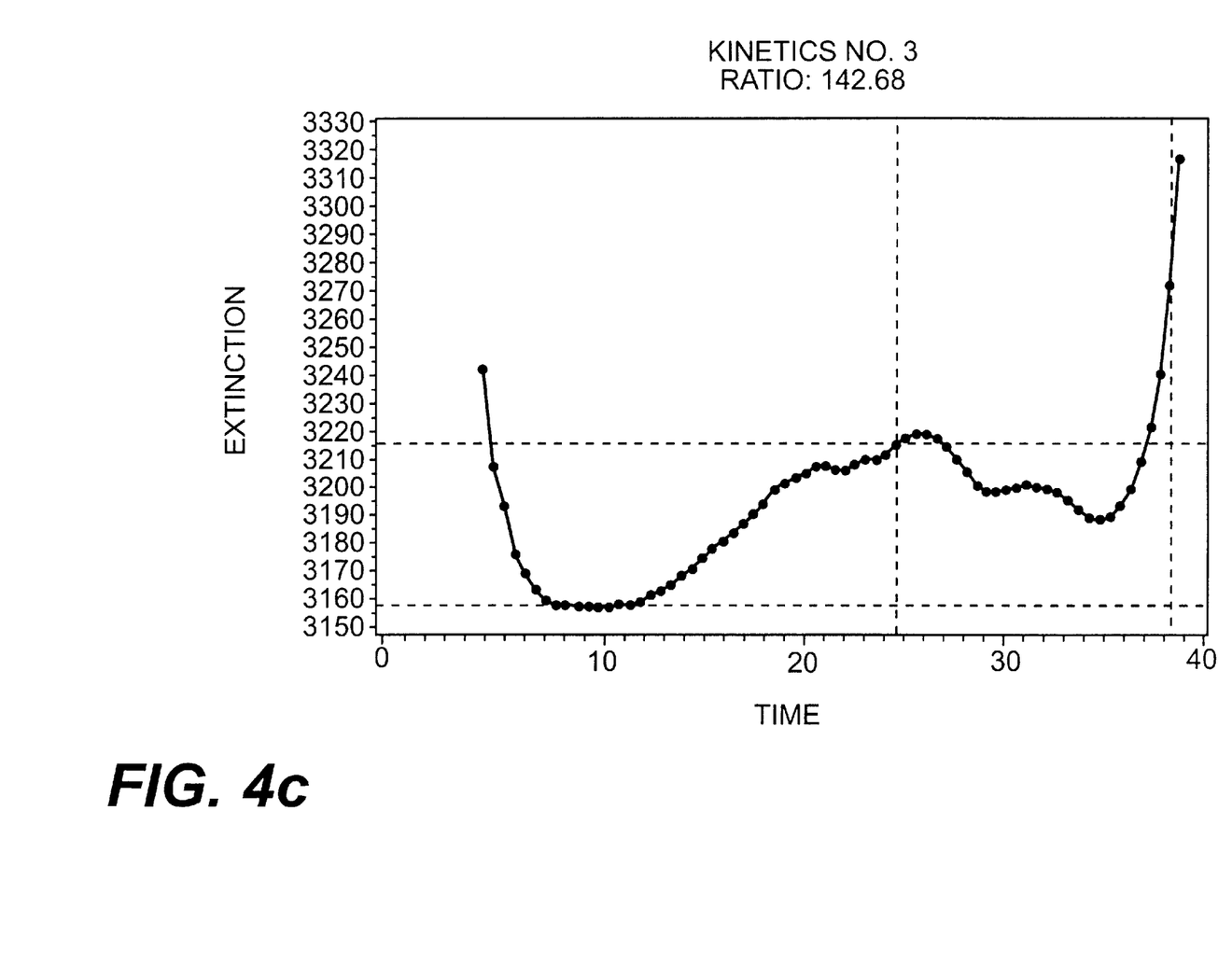
FIG. 4c: Extinction v. Time having Q=142.68.
Figure 4D:
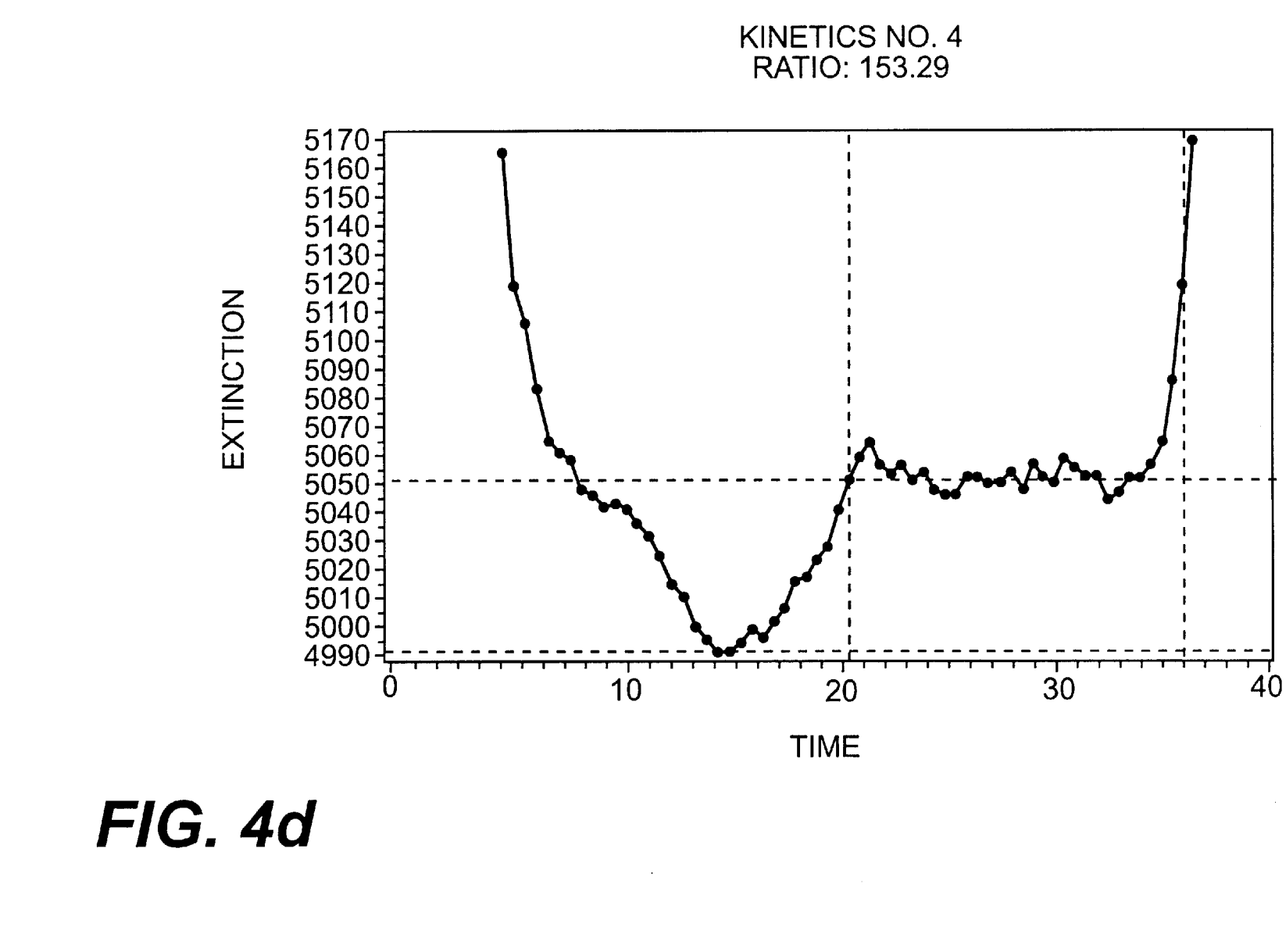
FIG. 4d: Extinction v. Time having Q=153.29.
Figure 4E:
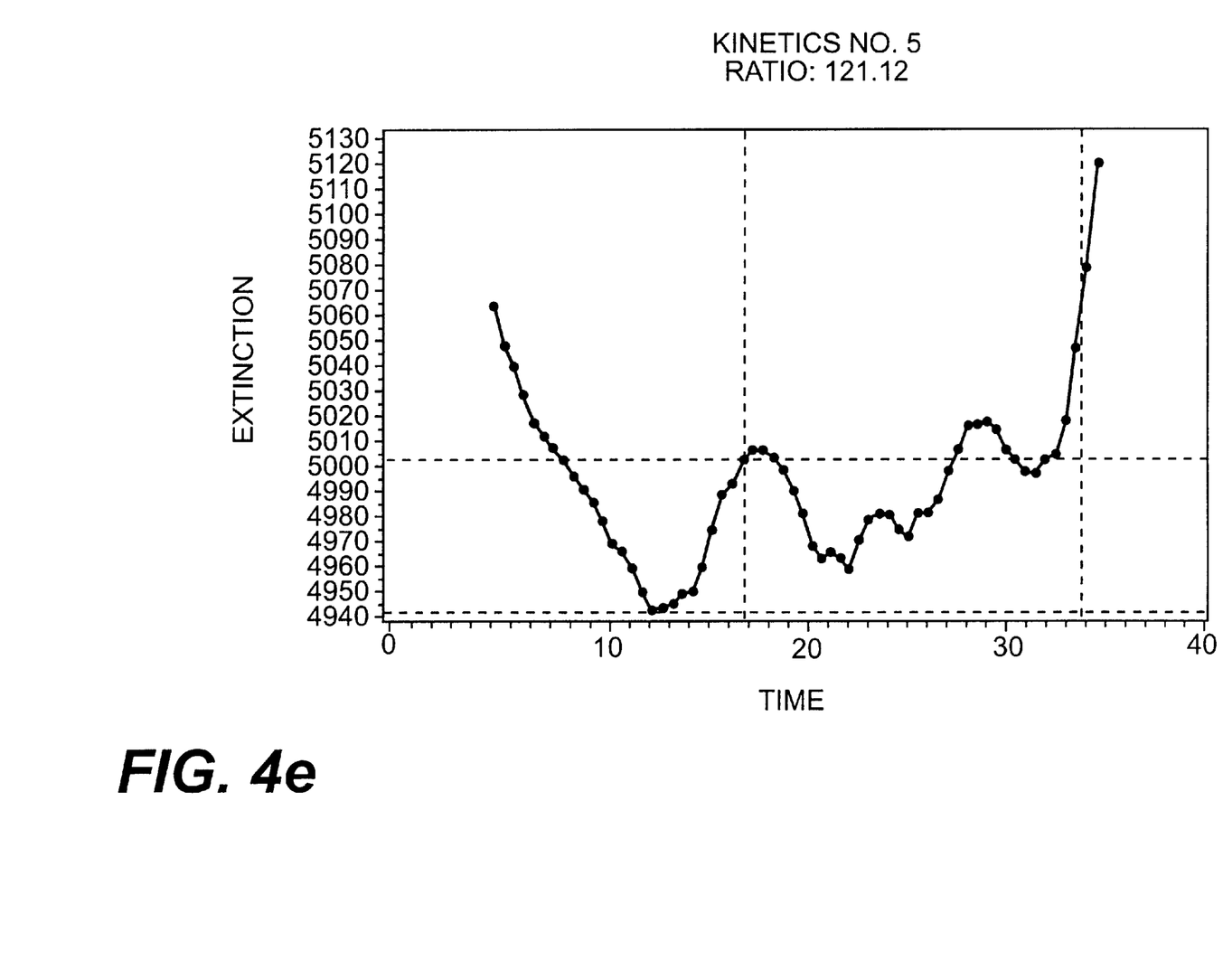
FIG. 4e: Extinction v. Time having Q=121.12.
Figure 4F:
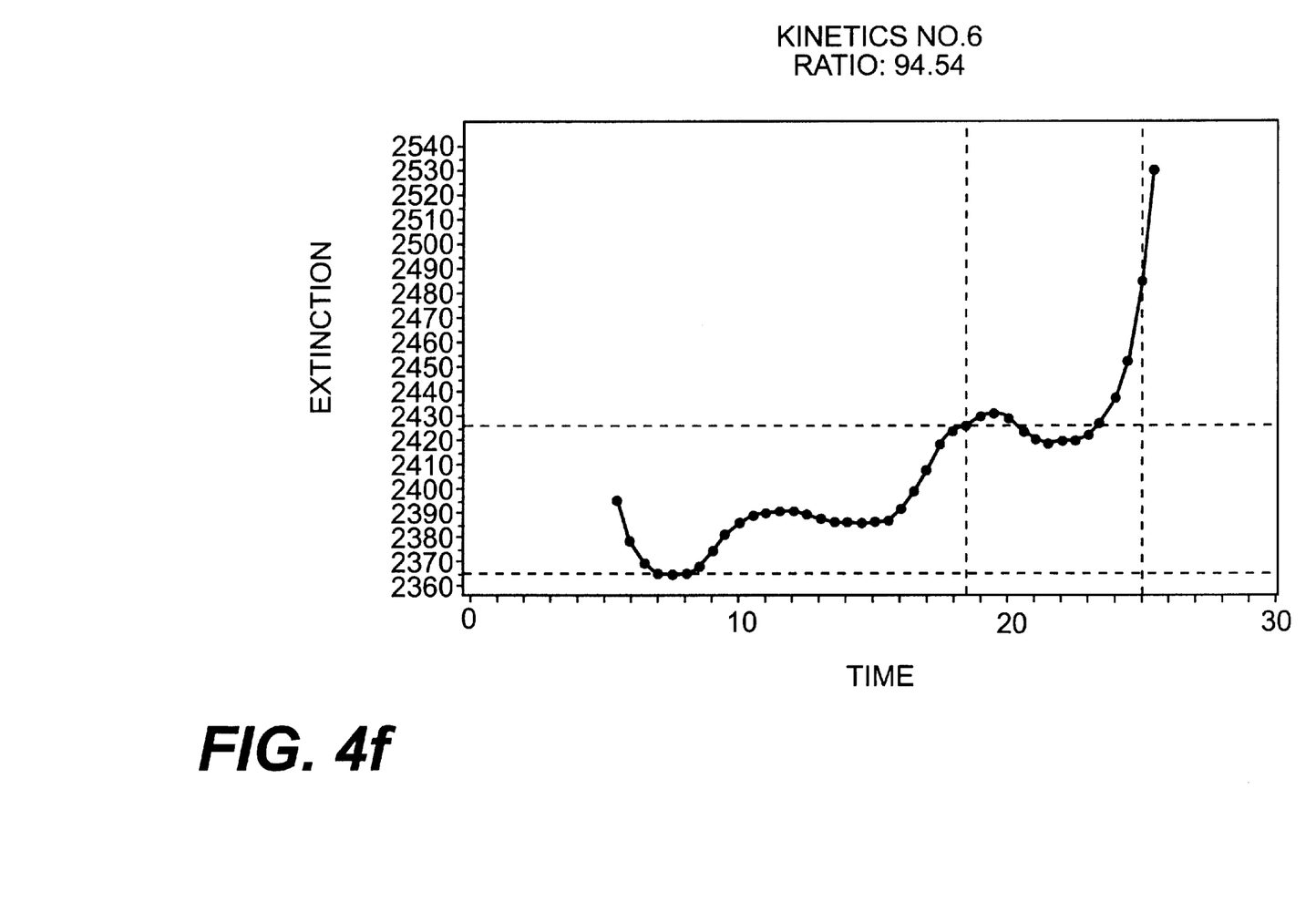
FIG. 4f: Extinction v. Time having Q=94.54.
Figure 4G:
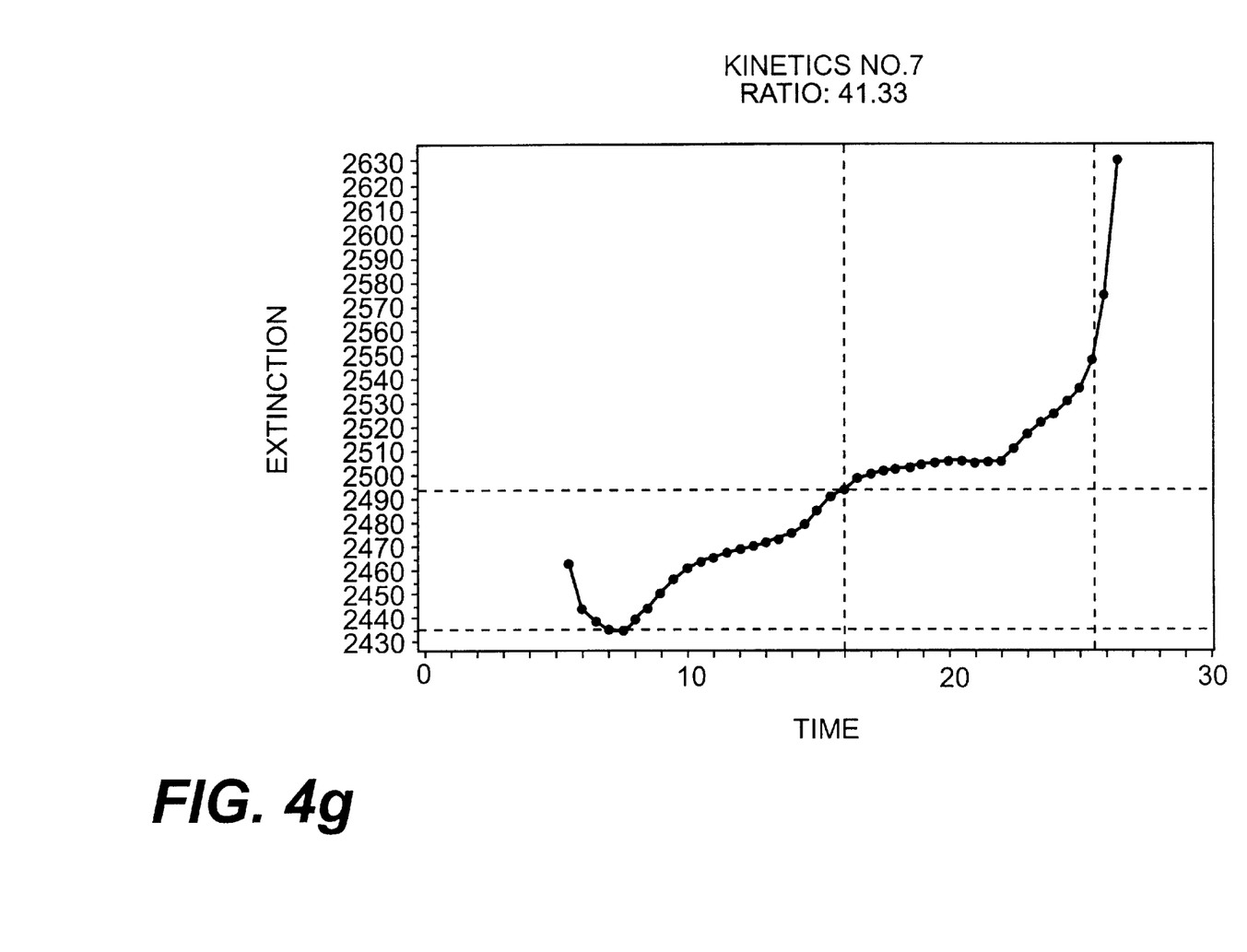
FIG. 4g: Extinction v. Time having Q=41.33.
Figure 4H:
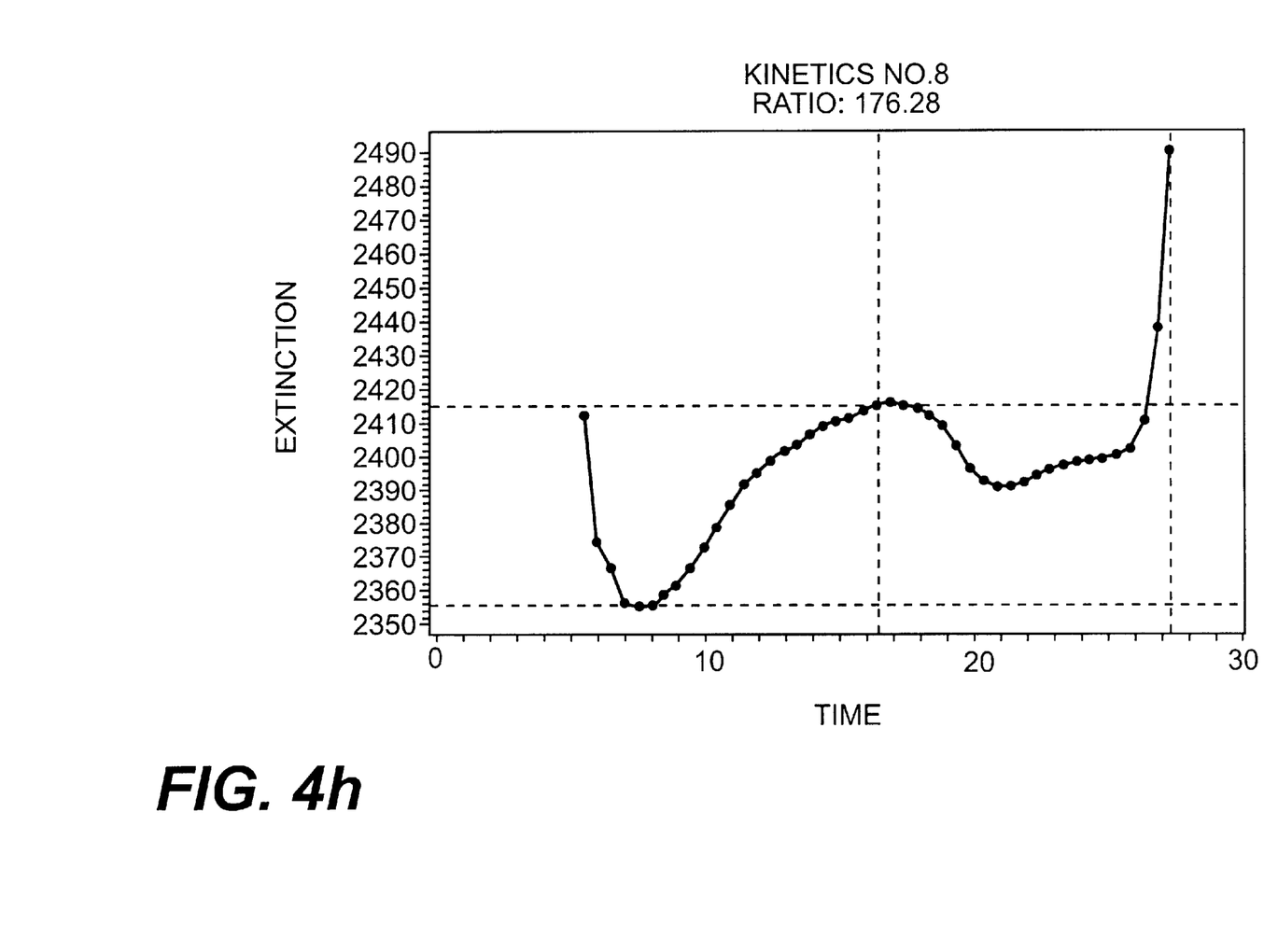
FIG. 4h: Extinction v. Time having Q=176.26.
Figure 4I:
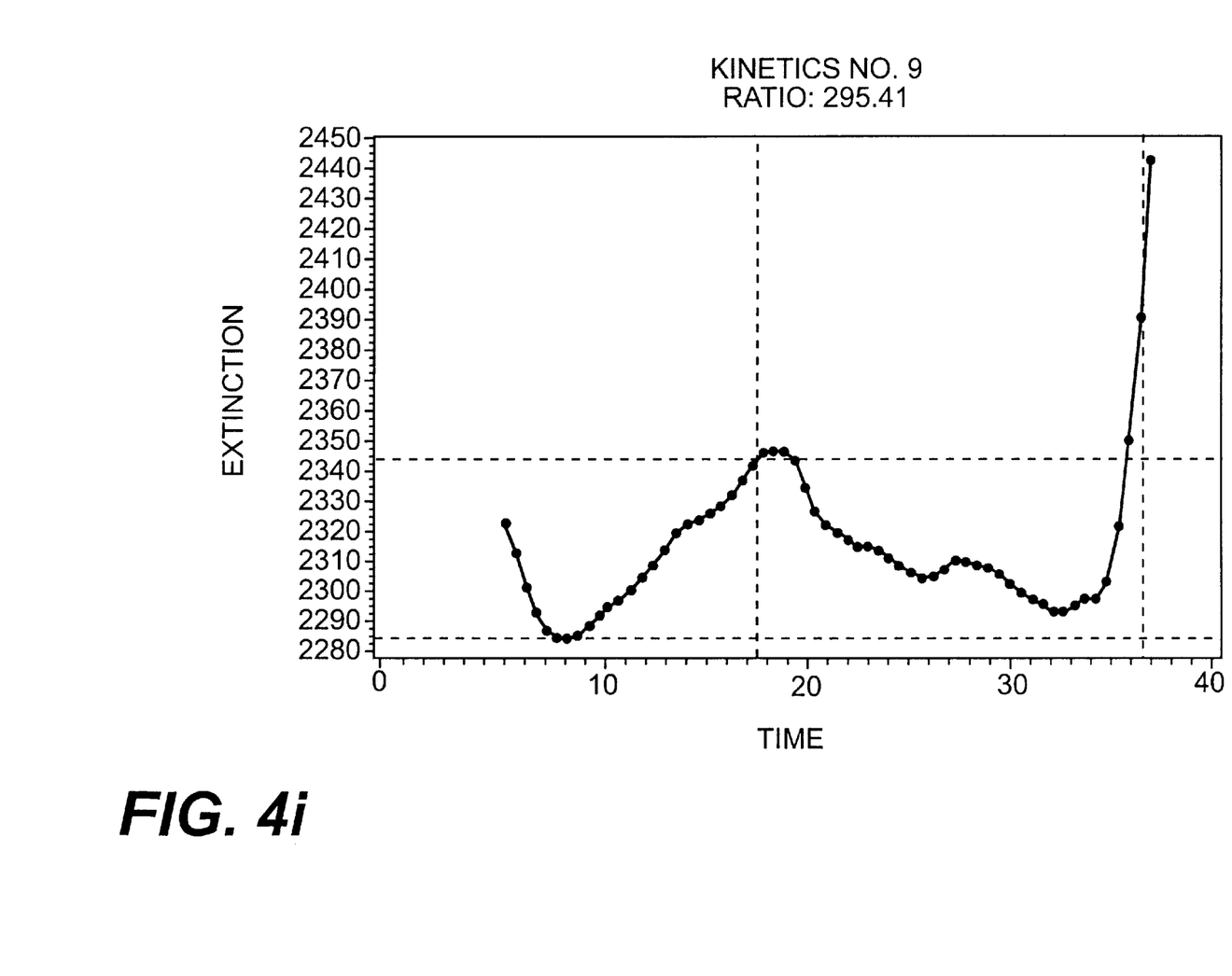
FIG. 4i: Extinction v. Time having Q=295.41.
Figure 4J:
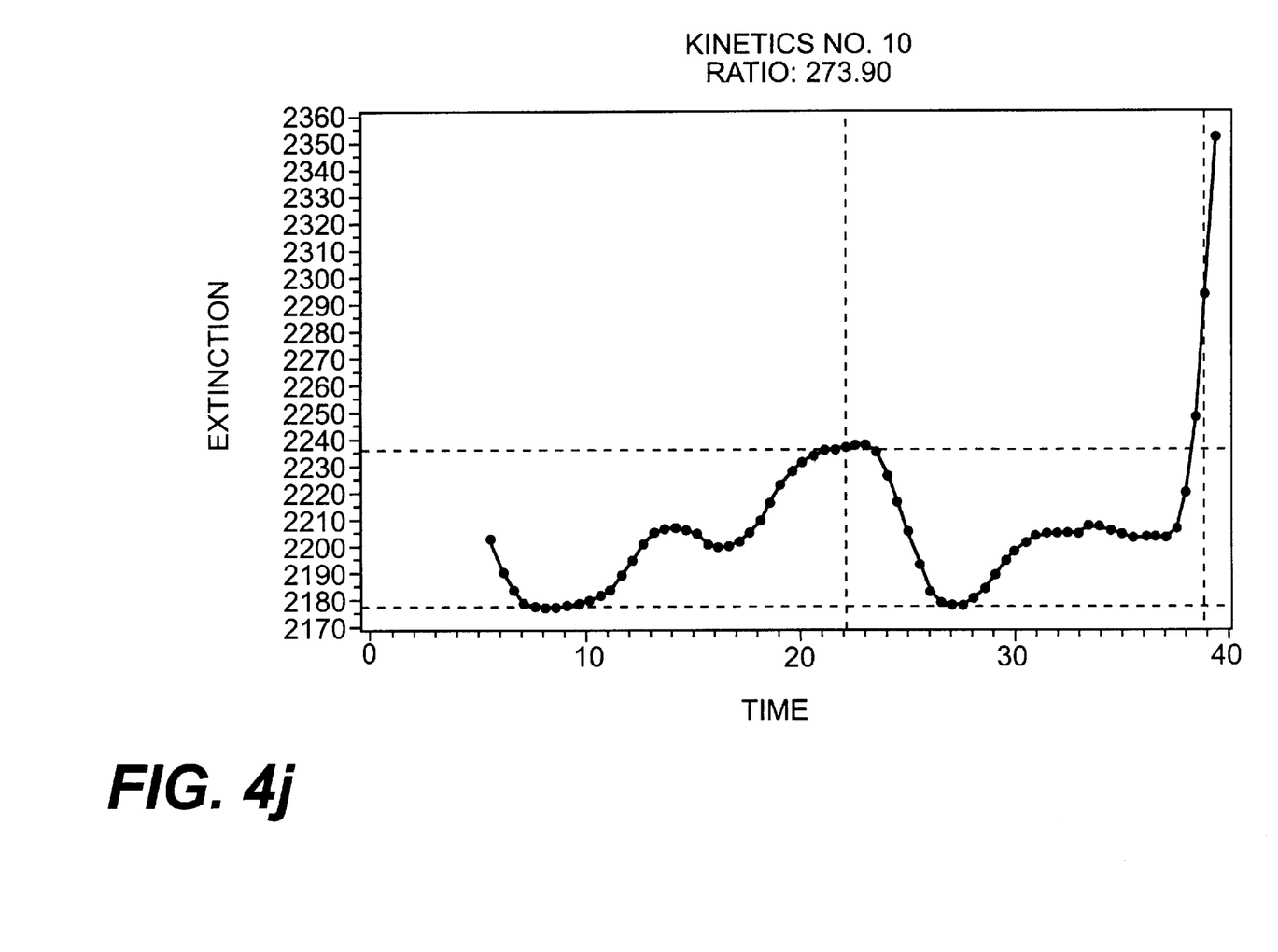
FIG. 4j: Extinction v. Time having Q=273.90.
Figure 4K:
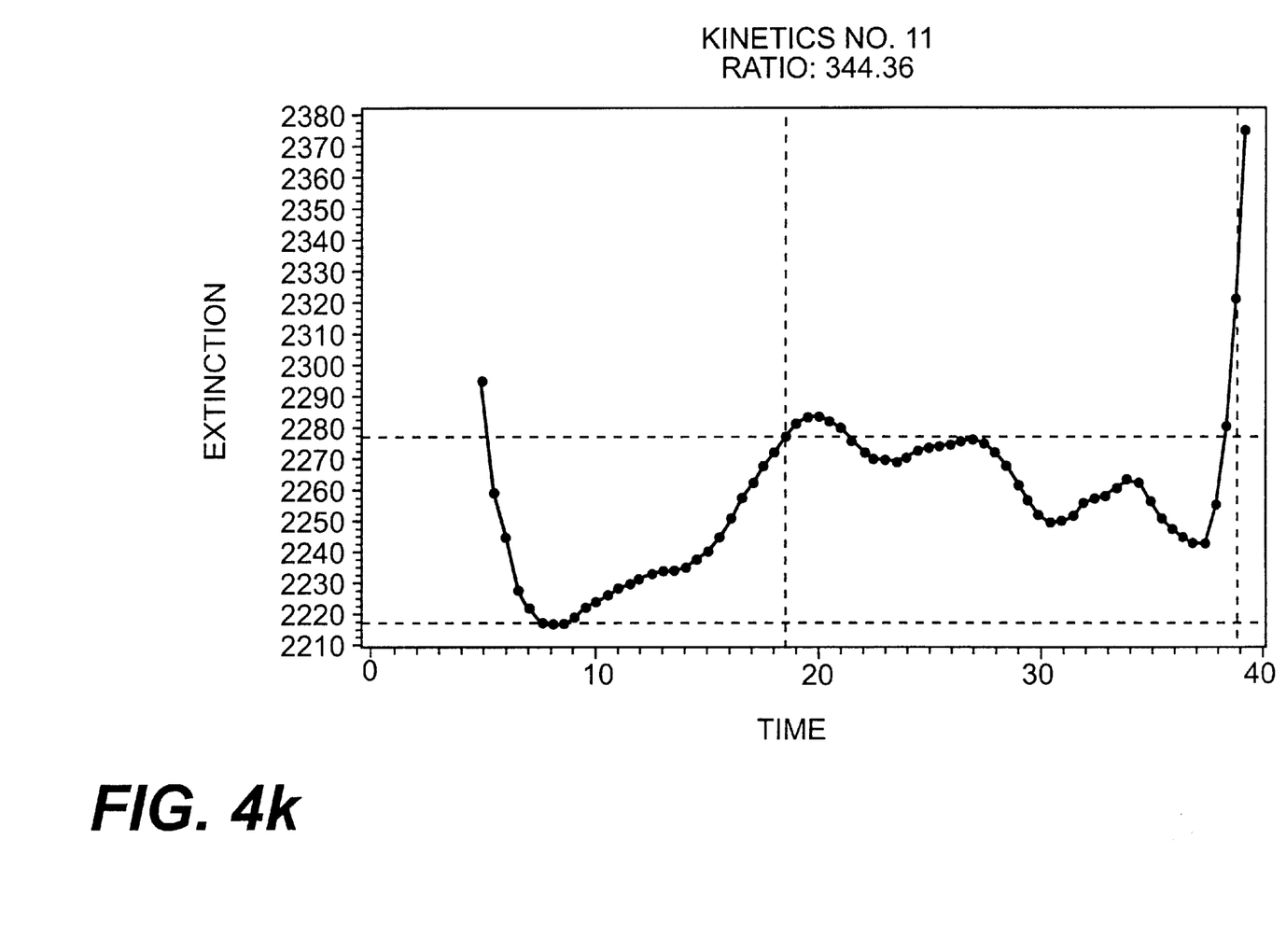
FIG. 4k: Extinction v. Time having Q=344.36.
Figure 4M:
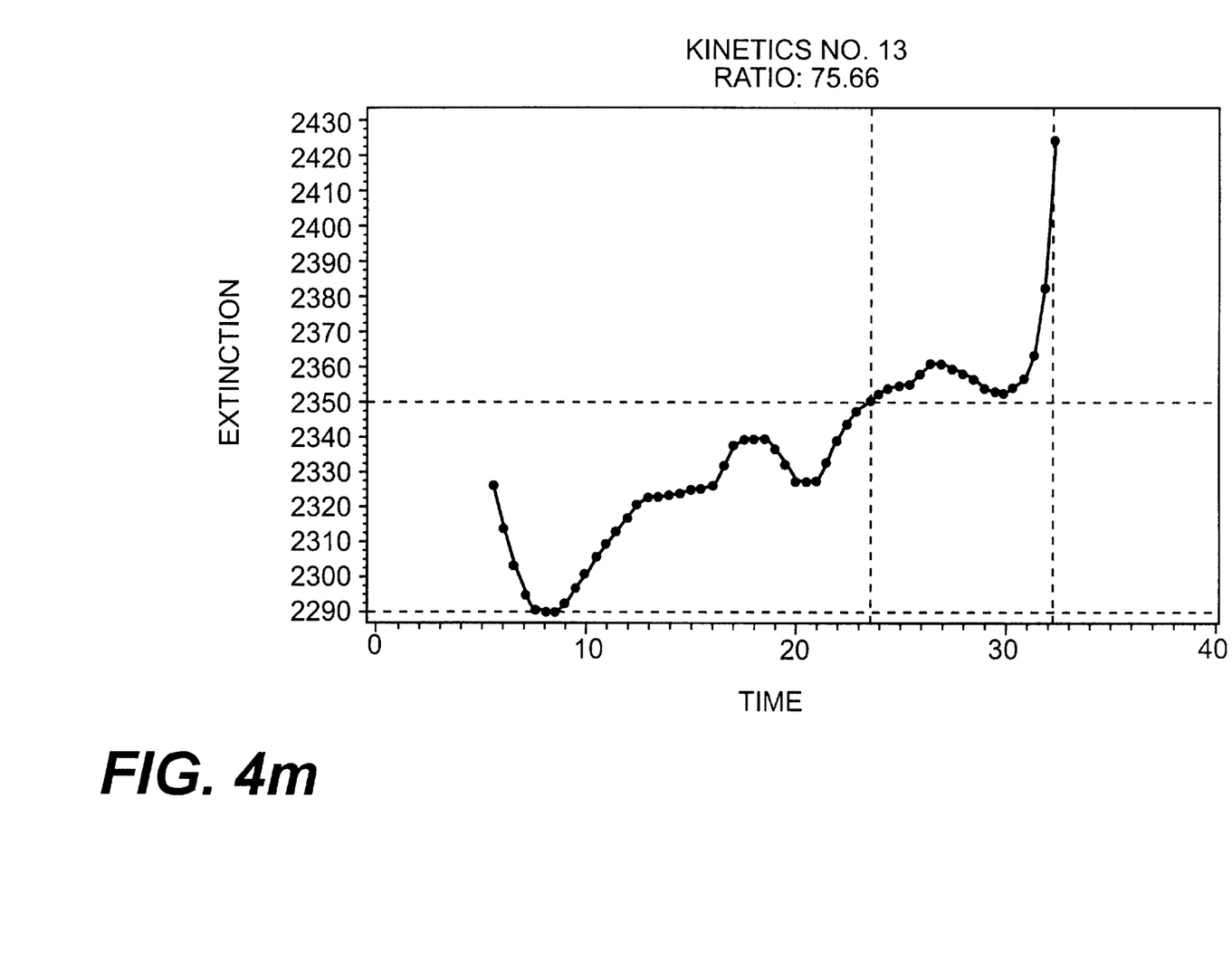
FIG. 4m: Extinction v. Time having Q=75.66.
Figure 4N:
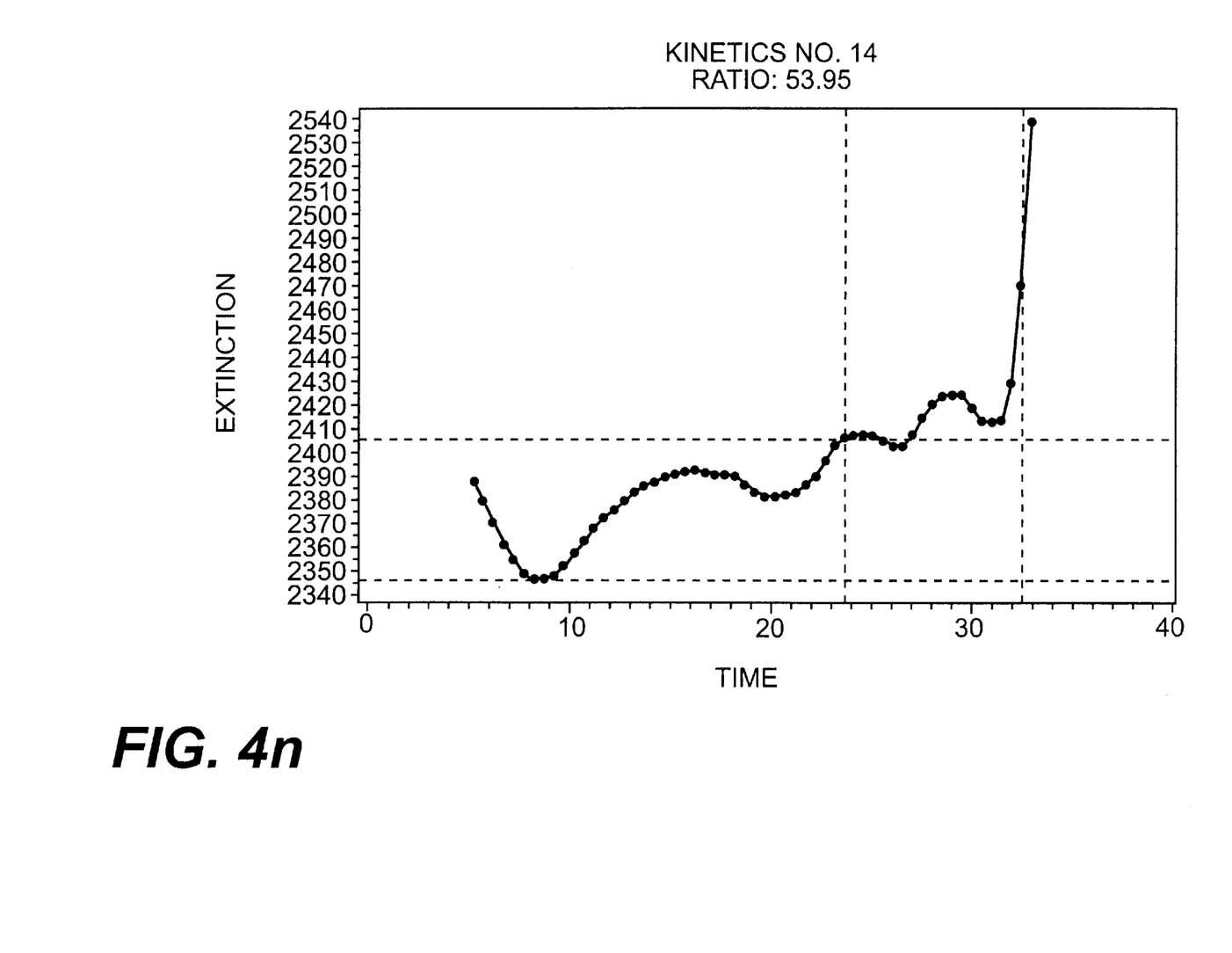
FIG. 4n: Extinction v. Time having Q=53.95.

The method according to the invention can be used both for $d_0$>0 and for $d_0$<0. In the case $d_0$<0 (decreasing kinetic process, FIG. 2), the same boundary conditions are valid as in the case of $d_0$>0 (FIG. 3).

The examples represented in FIG. 4 (a–n) are taken exclusively from the field of coagulation diagnosis. All were erroneously evaluated by the conventional threshold-value method using a threshold of 60. The minimum of the curve profile was in this case defined as the base value. The title of the graph gives the relevant ratio Q which results with the typical configuration specified above. With the limit of 20 specified there for the ratio all the profiles could accordingly be classed as critical. A subsequent therapeutic measure undertaken on the basis of the wrong raw values would almost certainly have led to life-threatening situations for the corresponding patients.

It is readily apparent to the appropriate person skilled in the art in other fields involving the evaluation of curve profiles that the method according to the invention can be carried over directly to these other fields. The method according to the invention can be applied to all measurements of a time-varying state of an object to be measured if this state is characterized by a rising or falling reaction curve, the time which is of interest being the one at which the system ceases to follow a predetermined path for the curve profile.

The method according to the invention can be used particularly advantageously in diagnostic methods. Relevant examples include:

diagnostic methods in which the time at which a particular state is entered is of interest (for example determination of plasma proteins, enzymatic reactions (for example ELISA))

chemical reaction profiles in which the time at which a particular state is entered is of interest.

The figures show the results of a series of PT (prothrombin time) determinations for a variety of patient sera. The dashed vertical line on the left gives the raw value (x-axis intercept) which would have been obtained using the conventional threshold-value method. The dashed vertical line on the right shows the correct raw value for the respective kinetic process.

EXAMPLES

The prothrombin times were determined for 14 patient plasmas from a clinic population. The prothrombin reagent Thromborel S (Behring Diagnostics GmbH, Order No. OUHP) was used with the Behring Coagulation System BCS, (Behring Diagnostics GmbH). The reagent was used in accordance with the manufacturer's instructions.

What is claimed is:

1. A method for evaluating reaction kinetics using the threshold-value method, in which the kinetics of a reaction are evaluated by measuring the change in a variable (S) which depends on the reaction, and measuring the time (T) taken for a limit value (d) to be exceeded, wherein the following steps are carried out:

(a) establishing values, specific to the reaction, of an initial value of $Q_0$, as well as $d_0$, a maximum value $d_{max}$ ($>d_0$), and a step number n, and hence a step size $d_s=(d_{max}-d_0)/n$;

(b) determining, for the range from $d_0$ to $d_{max}$, the value $T_n$ for each $d_n=(d_0+(d_s)*n)$, and $d_0$;

(c) determining, from the ordered series of values $T_0$ to $T_{max}$, the differences $D_i=T_i-T_{i-1}$ for i=1, . . . , n, and the largest value $D_{max}$ and the smallest value $D_{min}$ from the set $D_1, \ldots, D_n$, and taking the Ratio $Q=D_{max}/D_{min}$; and (d) using only a measurement for which $Q \leq Q_0$ for further evaluation.

2. The method as claimed in claim 1, wherein said measurement for which $Q>Q_0$ is also evaluated by taking the time $T_{max}$ associated with $d_{max}$ as the current measurement result.

3. The method as claimed in claim 2, in which the time $T_{max}$ associated with $d_{max}$ is taken as the current measurement result for each measurement.

4. An instrument for evaluating reaction kinetics, wherein the method for evaluating as claimed in claim 3 is installed at the hardware or software level.

5. A method for determining coagulation parameters, by adding a reaction partner, which leads to a parameter-dependent change in a variable (S), to a sample of a biological material, wherein the reaction kinetics are evaluated using the method as claimed in claim 3.

6. An instrument for evaluating reaction kinetics, wherein the method for evaluating as claimed in claim 2 is installed at the hardware or software level.

7. A method for determining coagulation parameters, by adding a reaction partner, which leads to a parameter-dependent change in a variable (S), to a sample of a biological material, wherein the reaction kinetics are evaluated using the method as claimed in claim 2.

8. The method as claimed in claim 1, in which the reaction is used to detect or determine a biological parameter or analyte.

9. The method as claimed in claim 8, the parameter being a coagulation parameter.

10. The method as claimed in claim 9, the parameter being the prothrombin time.

11. The method as claimed in claim 9 for determination of coagulation parameters.

12. An instrument for evaluating reaction kinetics, wherein the method for evaluating as claimed in claim 1 is installed at the hardware or software level.

13. A method for determining coagulation parameters, by adding a reaction partner, which leads to a parameter-dependent change in a variable (S), to a sample of a biological material, wherein the reaction kinetics are evaluated using the method as claimed in claim 1.

* * * * *